United States Patent
Chen et al.

(10) Patent No.: US 12,408,887 B2
(45) Date of Patent: Sep. 9, 2025

(54) PHANTOM-FREE CALIBRATION METHOD FOR A COMPUTERIZED TOMOGRAPHY SCAN

(71) Applicants: China Medical University, Taichung (TW); China Medical University Hospital, Taichung (TW)

(72) Inventors: Yi-Wen Chen, Taichung (TW); Cheng-Ting Shih, Taichung (TW); Yu-Fen Chen, Taichung (TW)

(73) Assignees: China Medical University, Taichung (TW); China Medical University Hospital, Taichung (TW)

( * ) Notice: Subject to any disclaimer, the term of this patent is extended or adjusted under 35 U.S.C. 154(b) by 317 days.

(21) Appl. No.: 18/353,306

(22) Filed: Jul. 17, 2023

(65) Prior Publication Data
US 2024/0115227 A1 Apr. 11, 2024

(30) Foreign Application Priority Data
Sep. 29, 2022 (TW) .................................. 111137080

(51) Int. Cl.
*A61B 6/58* (2024.01)
*A61B 6/03* (2006.01)

(52) U.S. Cl.
CPC .............. *A61B 6/582* (2013.01); *A61B 6/032* (2013.01)

(58) Field of Classification Search
CPC ......... A61B 6/582; A61B 6/032; A61B 6/583; A61B 6/505; A61B 6/482; A61B 6/5217; A61B 6/4042; A61B 6/4441; A61B 6/5235; A61B 6/5211; A61B 6/4241; A61B 6/585; A61B 6/4233; A61B 6/5205; A61B 6/5229; C08K 3/32; G16H 50/20; G09B 23/286; G09B 23/30; G06T 11/003;
(Continued)

(56) References Cited

U.S. PATENT DOCUMENTS

2004/0242987 A1* 12/2004 Liew ...................... G16H 50/30
600/407
2006/0056580 A1 3/2006 Frangioni et al.
(Continued)

FOREIGN PATENT DOCUMENTS

TW 202029213 A 8/2020

*Primary Examiner* — Irakli Kiknadze
(74) *Attorney, Agent, or Firm* — Best & Flanagan LLP

(57) ABSTRACT

A phantom-free calibration method for a computerized tomography scan has the steps of: scanning a plurality of homogeneous human tissues with a computerized tomography scanner and obtaining homogeneous human tissue scan information; scanning a tissue to be tested with the computerized tomography scanner and obtaining tissue to be tested scan information; calculating a spectral characteristic parameter of the computerized tomography scanner with a computing device using a model, wherein a standard tissue parameter of the homogeneous human tissues and the human tissue scan information are used in the model; and calculating a tissue parameter of the tissue to be tested with the computing device using the model, wherein the spectral characteristic parameter and the tissue to be tested scan information are inputted in the model. The phantom-free calibration method makes the tissue parameters of the tissue to be tested more accurate and the calibration process easier and more convenient.

5 Claims, 1 Drawing Sheet

(58) Field of Classification Search
CPC ......... G06T 11/005; G06T 2207/10081; G06T 2211/40; G01N 23/046; G01N 2223/3035; G01T 1/2985; G01T 1/169; G01T 7/005; G01T 1/161; G01T 1/171
See application file for complete search history.

(56) References Cited

U.S. PATENT DOCUMENTS

| | | | |
|---|---|---|---|
| 2008/0031412 A1* | 2/2008 | Lang | A61B 5/00 |
| | | | 378/54 |
| 2018/0113227 A1* | 4/2018 | Lin | G01T 1/169 |
| 2019/0317231 A1* | 10/2019 | Hofmann | G01T 7/005 |

* cited by examiner

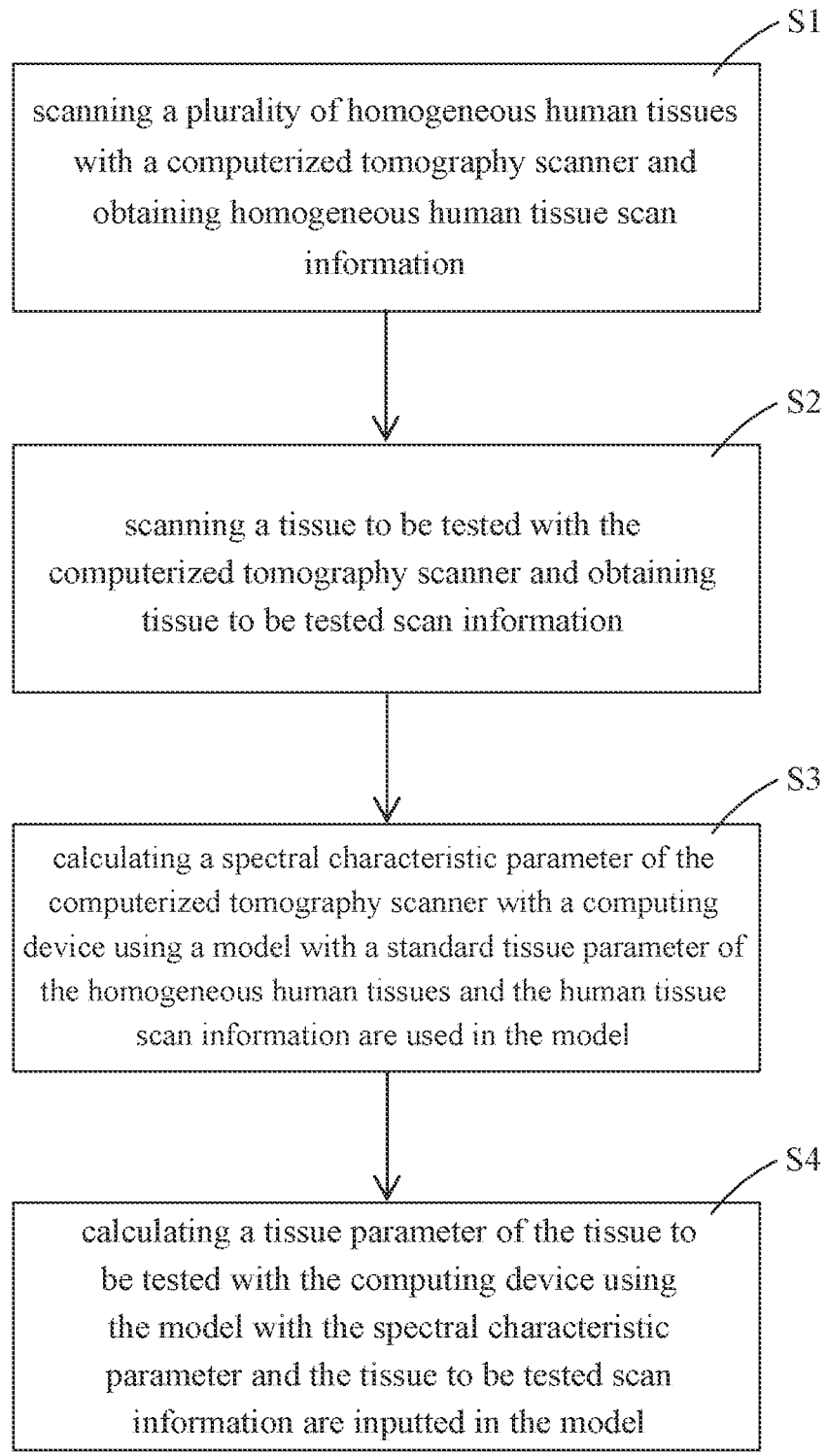

PHANTOM-FREE CALIBRATION METHOD FOR A COMPUTERIZED TOMOGRAPHY SCAN

FIELD OF INVENTION

The present invention relates to a calibration method.

BACKGROUND OF THE INVENTION

In radiotherapy dose planning, the physical parameters of the patient's tissue must be determined in order to calculate the dose to be administered. In dose planning for proton therapy, because the proton beam has a distinct energy release peak at a specific depth, called the Bragg peak, it is important to confirm the Bragg peak is at the correct depth for treatment. To determine the energy distribution of the proton beam in human tissue, it is possible to calculate the relative proton stopping power of the patient tissue, which is related to the physical parameters of the patient tissue. Therefore, it is important to understand the physical parameters of the patient tissue to calculate the relative proton stopping power in order to accurately calculate the energy release distribution of the proton beam in the tissue of the patient.

The current method is to scan a phantom in a computerized tomography (CT) scanner and to obtain a spectral characteristic parameter of the CT scanner by using and calculating the known tissue parameters of the phantom and the information obtained from the scan, i.e., the Hounsfield Unit (HU) of the CT, also known as the CT number, and then obtaining another CT number by scanning the patient's tissue to be tested with the CT scanner, obtaining the tissue parameters of the patient's tissue to be tested by this CT number and the spectral parameters, and using these tissue parameters to calculate the relative proton stopping power of the patient's tissue to be tested. However, this calibration method is cumbersome, and the elemental composition of the phantom and the human body are quite different, so scanning the phantom as a calibration method for the CT scanner may result in a discrepancy between the tissue parameters obtained by scanning the tissue to be tested and the actual tissue parameters, resulting in less accurate relative proton stopping power parameters of the tissue to be tested and reducing the effectiveness of proton therapy.

SUMMARY OF THE INVENTION

In order to improve the inconvenience of using a phantom to calibrate the CT scanner and the discrepancy between the elemental composition of the phantom and the human body, which leads to a large error in the obtained tissue parameters, the present invention provides a method for calibrating the CT scanner without using a phantom as a standard reference material.

A phantom-free calibration method for a computerized tomography scan of the present invention, comprising the steps of: scanning a plurality of homogeneous human tissues with a computerized tomography scanner and obtaining homogeneous human tissue scan information; scanning a tissue to be tested with the computerized tomography scanner and obtaining tissue to be tested scan information; calculating a spectral characteristic parameter of the computerized tomography scanner with a computing device using a model, wherein a standard tissue parameter of the homogeneous human tissues and the human tissue scan information are used in the model; and calculating a tissue parameter of the tissue to be tested with the computing device using the model, wherein the spectral characteristic parameter and the tissue to be tested scan information are inputted in the model.

Further, in the calibration method as described above, the homogeneous human tissue can be scanned simultaneously with the tissue to be tested by the CT scanner to obtain the homogeneous human tissue scan information and the tissue to be tested scan information; calculating a standard tissue parameter of the homogeneous human tissue and the homogeneous human tissue scan information in a model to obtain a spectral characteristic parameter of the CT scanner, and then calculating, by the computing device, the spectral characteristic parameter and the tissue to be tested scan information by inputting them into the model to obtain a tissue parameter of the tissue to be tested.

Further, in the calibration method as described above, the spectral characteristic parameter includes a Rayleigh scattering coefficient and a photoelectric absorption coefficient. By obtaining these coefficients, the spectral characteristics of the CT scanner can be understood, and thus the tissue parameters of the tissue to be tested can be obtained.

Further, the standard tissue parameters are the multiple parameters provided by the International Commission on Radiation Units and Measurements (ICRU) Report No. 44.

Since the present invention uses a variety of homogeneous human tissues as calibration calibration samples, it can make the tissue parameters of the tissues to be tested from the CT scan more closely resemble the real tissue parameters, which provides more accurate data for calculating the relative proton stopping power; and since it does not require the use of a phantom for calibration, it makes the process easier and more convenient.

BRIEF DESCRIPTION OF THE DRAWINGS

The present invention will be further illustrated by way of exemplary embodiments, which will be described in detail by way of the accompanying drawings. These embodiments are not limiting, and in these embodiments the same numbering indicates the same structure, wherein:

FIG. 1 is a schematic diagram of the flow of the method of the present invention.

DESCRIPTION OF THE PREFERRED EMBODIMENTS

As shown in FIG. 1, the scan information 10 of the phantom-free calibration CT scanner of the present invention is realized by the steps shown in the figure, but in other embodiments, the number of steps may be less or more, and the order of the steps may be adjusted, such that the number and order of the steps are not limited to those described in this embodiment.

As indicated in the present invention and the claims, unless the context clearly suggests otherwise, the terms "a", "one", "a kind of", and/or "the" do not specifically refer to the singular, but may also include the plural. In general, the terms "includes" and "contains" suggest only the inclusion of clearly identified steps and elements that do not constitute an exclusive list, and the method or apparatus may include other steps or elements.

It should be understood that "homogeneous human tissue" as used herein refers to a human tissue or organ that is homogeneous in composition of elements within a range, or that contains a homogeneous proportion of water, protein, and fat, or that has similar characteristics and functions.

However, if other terms can accomplish the same purpose, said terms may be substituted by other expressions.

Step S1: Scanning a plurality of homogeneous human tissues with a CT scanner and obtaining homogeneous human tissue scan information;

Step S2: Scanning a tissue to be tested with the CT scanner and obtaining tissue to be tested scan information;

Step S3: Calculating a spectral characteristic parameter of the computerized tomography scanner with a computing device using a model, wherein a standard tissue parameter of the homogeneous human tissues and the human tissue scan information are used in the model; and Step S4: Calculating a tissue parameter of the tissue to be tested with the computing device using the model, wherein the spectral characteristic parameter and the tissue to be tested scan information are inputted in the model.

Further, Steps S1 and S2 can be performed simultaneously, and the homogeneous human tissue with known tissue parameters and the scan information of the tissue to be tested can be obtained in the same scan of the CT scanner; calculating a standard tissue parameter of the homogeneous human tissue and the homogeneous human tissue scan information in a model to obtain a spectral characteristic parameter of the CT scanner, and then calculating, by the computing device, the spectral characteristic parameter and the tissue to be tested scan information by inputting them into the model to obtain a tissue parameter of the tissue to be tested.

Further, the spectral characteristics parameter includes a Rayleigh scattering coefficient and a photoelectric absorption coefficient.

Further, the model includes:

$$\frac{CTN_m}{1000} + 1 =$$

$$\frac{\mu_m}{\mu_{H_2O}} = \frac{\rho_m}{\rho_{H_2O}} \frac{\sum_{i=1}^{N}\left(\frac{w_i}{A_i}\right)\left(Z_i + Z_i^{d+1} \cdot k_1^{sn} + Z_i^{a+1} \cdot k_2^{sn}\right)}{\left(\frac{w_H}{A_H}\right)\left(k_1^{sn} + k_2^{sn} + 1\right) + \left(\frac{w_O}{A_O}\right)\left(8^{d+1} \cdot k_1^{sn} + 8^{a+1} k_2^{sn} + 8\right)}$$

$CTN_m$ is a scan information obtained after scanning by the CT scanner, $\mu_m$ is the light attenuation coefficient of a tissue, $\mu_{H_2O}$ is the light attenuation coefficient of water, $\rho_m$ is the density of the tissue, $\rho_{H_2O}$ is the density of water, $w_i$ is the mass fraction of an element in the tissue, $A_i$ is the molecular weight of the element in the tissue, $Z_i$ is the atomic number of the element, a and d are fitting parameters, $w_H$ is the mass proportion of hydrogen in water, $A_H$ is the atomic weight of hydrogen in water, $w_O$ is the mass proportion of oxygen in water, $A_O$ is the atomic weight of oxygen in water, $k_1^{s_n}$ is the Rayleigh scattering coefficient of the CT scanner, $k_2^{s_n}$ is the photoelectric absorption coefficient of the CT scanner.

EMBODIMENT

In this embodiment, a plurality of homogeneous human tissues such as a cortical bone, an adipose tissue, blood, and a muscle tissue, and air are used as calibration samples for calibrating the scan information of the CT scanner. Wherein the plural homogeneous human tissues are not limited to the human tissues used in this embodiment, but a variety of other homogeneous human tissues may be used as the calibration sample for calibrating the scan information of the CT scanner. In another embodiment, the homogeneous human tissue is a variety of non-skeletal tissues for which tissue information is available in ICRU Report No. 44.

In this embodiment, the cortical bone, adipose tissue, blood, muscle tissue, and air are taken directly from the same CT image of the same subject (i.e., the homogeneous human tissues are from the same patient as the patient of the tissue to be tested, in other words, the patient goes through one CT scan), and the scan information is read from the scan image with respect to the homogeneous human tissues and air.

Using the scan information of the adipose tissue and the cortical bone tissue and the tissue parameters to obtain a spectral characteristic parameter of the CT scanner; reading the scan information of the tissue to be tested in the same scan image; and using the spectral characteristic parameter and the scan information to obtain the tissue parameters of the tissue to be tested.

COMPARATIVE EXAMPLE

In the comparative example, a phantom (in this embodiment, a tissue-equivalent phantom manufactured by Gammex RMI Ltd.) corresponding to a cortical bone, an adipose tissue, two lungs, a breast, a brain, a liver, four skeletal tissues with different bone densities, water, and solid water is used as a standard reference material for calibration of the CT scanner scan information.

Scanning the phantom with a CT scanner to obtain scan information.

Combining the tissue parameters of the phantom with the scan information to obtain the spectral characteristic parameters of the tissue to be tested.

Scanning the tissue to be tested with the CT scanner and using the obtained scan information and the spectral characteristic parameters to obtain a tissue parameter of the tissue to be tested.

Comparison of Embodiment and Comparative Example

Table 1 shows the weight percentages of the elemental composition of adipose tissue, cortical bone phantom and human body. From the table, it can be seen that the composition of the phantom and the homogeneous human tissues still differ to some extent. For example, in the adipose tissue, the percentage of carbon elements in the phantom is significantly higher than the percentage of carbon elements in the human adipose tissue, while the percentage of oxygen elements in the human adipose tissue is significantly higher than the percentage of oxygen elements in the phantom. Similar differences were found in cortical bone, and the phantom lacked the phosphorus element of human cortical bone.

TABLE 1

Weight percentages of human and phantom element composition of adipose and cortical bone

| | Element | H | C | N | O | Na | Mg | P | S | Cl | Ca |
|---|---|---|---|---|---|---|---|---|---|---|---|
| Adipose Tissue | Phantom [a] | 9.1 | 72.3 | 2.3 | 16.3 | | | | | | |
| | Human Body [b] | 11.4 | 59.87 | 0.73 | 27.7 | 0.1 | | | 0.1 | 0.1 | |
| Cortical Bone | Phantom [a] | 3.4 | 31.4 | 1.8 | 36.5 | | | | | | 26.8 |
| | Human Body [b] | 3.4 | 15.5 | 4.2 | 43.5 | 0.1 | 0.2 | 10.3 | 0.3 | | 22.5 |

[a] Data provided by Gammex RMI Ltd.
[b] Data provided by ICRU Report No. 44

From the analysis of the elemental composition of the phantom and the human body, it is clear that the elemental composition of the phantom is still very different from that of the human body, and using the phantom as a calibration for the spectral characteristic parameters of the CT scanner to obtain the tissue parameters of the tissue to be tested may lead to significant deviations, especially when the tissue parameters are used for proton therapy.

The following equation will be used to calculate the relative proton stopping power of the embodiment and the comparative example, wherein:

$$RPSP_m = \rho_e \frac{\ln\left[\frac{2m_0 c^2 \beta^2}{I_m(1-\beta^2)}\right] - \beta^2}{\ln\left[\frac{2m_0 c^2 \beta^2}{I_{water}(1-\beta^2)}\right] - \beta^2}$$

$RPSP_m$ is the relative proton stopping power, $\rho_e$ is the electron density, $m_0$ is the net mass of electrons, c is the speed of light, $\beta$ is the ratio of proton motion velocity to the speed of light, $I_m$ is the average excitation energy of tissue, and $I_{water}$ is the average excitation energy of water; the calculation results are shown in Table 2.

TABLE 2

Differences between the tissue parameters and the ICRU 46 standard obtained by the calibration method of the comparative example and the embodiment

| Calibration Method | Adipose Tissue Relative Proton Stopping Power | Average Absolute Percentage Error | Cortical Bone Relative Proton Stopping Power | Average Absolute Percentage Error |
|---|---|---|---|---|
| ICRU[a] | 0.96904 | — | 1.69764 | — |
| Phantom | 0.911604 | 5.90% | 1.776733 | 4.70% |
| Phantom-free | 0.957398 | 1.20% | 1.685408 | 0.70% |

[a] Data provided by ICRU Report No. 46

As can be seen from Table 2, the relative proton stopping power and ICRU data obtained by the phantom-free CT scan calibration method of the present invention have a smaller error than those obtained by the phantom calibration. For example, in the case of adipose tissue, the average absolute percentage error of the relative proton stopping power and ICRU data obtained with the phantom calibration CT scanner is up to 5.90%, while the average absolute percentage error of the phantom-free calibration method of the embodiment is only 1.20%; and similar results are obtained for cortical bone, where the average absolute percentage error of the relative proton stopping power and ICRU Report No. 46 data obtained with the phantom calibration CT scanner is as high as 4.70%, while the average absolute percentage error of the phantom-free calibration method of the embodiment is only 0.70%. The calibration method of the embodiment is better than that of the phantom calibration method in all aspects.

With the foregoing description, it can be seen that the present invention achieves the following effects:

The use of known homogeneous human tissues as calibration samples for calibration of the CT scanner can provide more accurate tissue parameters of the tissues being tested than the use of a phantom; and the calibration process can be simplified by eliminating the use of a phantom.

What is claimed is:

1. A phantom-free calibration method for a computerized tomography scan, comprising steps of:
   scanning a plurality of homogeneous human tissues with a computerized tomography scanner and obtaining homogeneous human tissue scan information;
   scanning a tissue to be tested with the computerized tomography scanner and obtaining tissue to be tested scan information;
   calculating a spectral characteristic parameter of the computerized tomography scanner with a computing device using a model, wherein a standard tissue parameter of the homogeneous human tissues and the human tissue scan information are used in the model; and
   calculating a tissue parameter of the tissue to be tested with the computing device using the model, wherein the spectral characteristic parameter and the tissue to be tested scan information are inputted in the model.

2. The method according to claim 1, wherein the homogeneous human tissue is scanned simultaneously with the tissue to be tested with the CT scanner to obtain the homogeneous human tissue scan information and the tissue to be tested scan information.

3. The method according to claim 1, wherein the spectral characteristic parameter comprises a Rayleigh scattering coefficient and a photoelectric absorption coefficient.

4. The method according to claim 1, wherein the model comprises:

$$\frac{CTN_m}{1000} + 1 =$$

$$\frac{\mu_m}{\mu_{H_2O}} = \frac{\rho_m}{\rho_{H_2O}} \frac{\sum_{i=1}^{N} \left(\frac{w_i}{A_i}\right)\left(Z_i + Z_i^{d+1} k_1^{sn} + Z_i^{a+1} \cdot k_2^{sn}\right)}{\left(\frac{w_H}{A_H}\right)\left(k_1^{sn} + k_2^{sn} + 1\right) + \left(\frac{w_O}{A_O}\right)\left(8^{d+1} \cdot k_1^{sn} + 8^{a+1} k_2^{sn} + 8\right)}$$

wherein: $CTN_m$ is a scan information obtained after scanning by the CT scanner, $\mu_m$ is the light attenuation coefficient of a tissue, $\mu_{H_2O}$ is the light attenuation coefficient of water, $\rho_m$ is the density of the tissue, $\rho_{H_2O}$ is the density of water, $w_i$ is the mass fraction of an element in the tissue, $A_i$ is the molecular weight of the element in the tissue, $Z_i$ is the atomic number of the element, a and d are fitting parameters, $w_H$ is the mass proportion of hydrogen in water, $A_H$ is the atomic weight of hydrogen in water, $w_O$ is the mass proportion of oxygen in water, $A_O$ is the atomic weight of oxygen in water, $k_1^{s_n}$ is the Rayleigh scattering coefficient of the CT scanner, $k_2^{s_n}$ is the photoelectric absorption coefficient of the CT scanner.

5. The method according to claim 1, wherein the standard tissue parameters are multiple parameters provided by the International Commission on Radiation Units and Measurements (ICRU) Report No. 44.

* * * * *